United States Patent [19]

Mathiowitz et al.

[11] Patent Number: 4,861,627
[45] Date of Patent: Aug. 29, 1989

[54] PREPARATION OF MULTIWALL POLYMERIC MICROCAPSULES

[75] Inventors: Edith Mathiowitz, Brookline; Robert S. Langer, Somerville, both of Mass.

[73] Assignee: Massachusetts Institute of Technology, Cambridge, Mass.

[21] Appl. No.: 45,840

[22] Filed: May 1, 1987

[51] Int. Cl.[4] .................. A61K 9/56; A61K 9/58; B01J 13/02
[52] U.S. Cl. ..................... 427/213.31; 264/4.3; 264/4.32; 264/4.6; 424/462; 424/497; 427/213.36; 428/402.22; 428/402.24; 514/963
[58] Field of Search .............. 264/4.3, 4.32, 4.6; 427/213.31, 213.36; 424/462, 497; 514/963

[56] References Cited

U.S. PATENT DOCUMENTS

| | | | |
|---|---|---|---|
| 3,523,906 | 8/1970 | Vrancken et al. | 264/4.6 |
| 3,640,892 | 2/1972 | Purcell | 264/4.6 |
| 3,691,090 | 9/1972 | Kitajima et al. | 264/4.6 |
| 3,830,750 | 8/1974 | Wellman | 264/4.6 |
| 3,859,228 | 1/1975 | Morishita et al. | 427/213.36 |
| 3,960,757 | 6/1976 | Morishita et al. | 427/213.36 |
| 4,187,194 | 2/1980 | Wellman et al. | 264/4.6 |
| 4,272,398 | 6/1981 | Jaffe | 427/213.31 |
| 4,637,905 | 1/1987 | Gardner | 264/4.3 |

OTHER PUBLICATIONS

Mathiowitz et al., J. Appl. Polymer Sci. 26, 809–822 (1981).
Mathiowitz et al., J. Controlled Release 5, 13–22 (1987).
Mathiowitz et al., Proceedings International Symposium of Controlled Release by Active Material 12, 183–184 (Jul. 1985).

*Primary Examiner*—Richard D. Lovering
*Attorney, Agent, or Firm*—Kilpatrick & Cody

[57] ABSTRACT

A single step method for preparation of multi-layer polymeric delivery systems. Any two or three different degradable or non-degradable polymers which are not soluble in each other at a particular concentration, as dictated by their phase diagram, can be used. The multilayer microcapsules produced by the method are distinguished by extremely uniform dimensioned layers of polymer and actual incorporation of the substance to be delivered into the polymer layers.

In the preferred embodiment of the method, two polymers are dissolved in a volatile organic solvent, the substance to be encapsulated is dispersed or dissolved in the polymer solution, the mixture is suspended in an aqueous solution and stirred, and the solvent is slowly evaporated, creating microspheres with an inner core formed by one polymer and an outer layer formed by the second polymer. In another embodiment one polymer may be formed within a layer of the other polymer by increasing the rate of evaporation of the volatile solvent.

14 Claims, 2 Drawing Sheets

PREPARATION OF MULTIWALL POLYMERIC MICROCAPSULES

BACKGROUND OF THE INVENTION

The United States Government has certain rights in this invention pursuant to National Institute of Health Grant No. NIH-5-RO1-GM26698.

The present invention is a new method for preparing multiwall polymer microspheres, particularly for use in controlled delivery systems.

Controlled delivery of substances such as drugs, insecticides, fertilizers, indicators, etc. can be achieved by a variety of processes. In one type of delivery system, a polymeric capsule is formed around or incorporating the substance to be delivered. The form and composition of the polymer or polymers determines the method that can be used to encapsulate the substance, the environment in which the capsule can be used, and the type of substance which can be encapsulated.

One process for preparing microspheres is a hot-melt technique. The melted polymer is mixed with the drug and the mixture suspended in a nonsolvent where it is cooled and solidified. The big disadvantage of this process is that only low melting polymers can be used with thermolabile substances.

An alternative method is the solvent evaporation technique, disclosed, for example, by U.S. Pat. No. 3,523,906 to M. N. Vrancken and U.S. Pat. No. 3,960,757 to M. Morishita. These processes have been used extensively to prepare microspheres from biodegradable polymers, as reported in the literature and by H. Jaffe in U.S. Pat. No. 4,272,398. The procedure consists of dissolving a polymer in methylene chloride or other volatile solvent. The drug is then either dissolved or suspended in the solution and the resulting mixture is emulsified in an aqueous phase containing an emulsifier. The solvent is allowed to evaporate to produce microspheres containing the substance to be encapsulated.

Yet another method used to form microcapsules is phase separation. Essentially, a polymer is forced to precipitate around a core by addition of non-solvent or by addition of a second polymer with is incompatible with the second polymer.

While all of these methods are useful in making microspheres for controlled delivery, they have certain disadvantages. For example, they do not always yield uniform polymer layers. The best one can do at present is to dip microspheres formed of one polymer into a bath of a second polymer and hope each microsphere is coated. In practice, the coatings tend to be non-uniform both with respect to coverage and to thickness. This can be fatal to a system for controlled delivery, as in controlled drug delivery systems requiring linear release of the drug as the polymer degrades in vivo. Further, many of these methods require multiple steps, with increasing quality control problems at each stage. The final yield is frequently low.

Even the fluidized bed method of forming a polymer coating around tablets, where uniform coatings are achievable, has disadvantages. Here, the substance to be incorporated cannot be mixed directly into the coating, especially when the substance is in particle form.

It is therefore an object of the present invention to provide a one step method for manufacturing delivery systems consisting of two or more polymers in microcapsule form.

It is a further object of the present invention to provide a method for manufacturing polymeric devices from a variety of polymers, including both biodegradable and non-biodegradable polymers.

It is another object of the present invention to provide a method for making polymeric delivery devices where substances in particle form can be incorporated directly into the polymers and which can be conducted at relatively low temperatures to avoid damaging any thermobile substances to be incorporated.

SUMMARY OF THE INVENTION

A single step method for preparation of multilayer polymeric drug delivery devices.

In the preferred embodiment of the method, two polymers are dissolved in a volatile organic solvent, the drug is dispersed or dissolved in the polymer solution, the mixture is suspended in an aqueous solution and stirred, and the solvent is slowly evaporated, creating microspheres with an inner core formed by one polymer and an outer layer of the second polymer.

In another embodiment, each of the polymers is dissolved in organic solvent and then mixed together. By selecting the appropriate solvents, the two solutions will not be soluble in each other and a suspension or emulsion will result. This insoluble mixture is then suspended in yet another solution, such as water, in which neither is soluble, and the solvents removed by evaporation.

In a further embodiment, the solvents are evaporated rapidly to produce spheres of the first polymer within a layer of the second polymer. The rate can be varied to form layers of each polymer with spheres within one polymer layer or to have all of one polymer in the form of spheres within the layer of the second polymer.

The important parameters for producing multilayered capsules of the desired composition are: the selection of the polymers, including the purity and the molecular weights of the selection, the solvent, the solubility and concentration of the polymers in the solvent, the selection and composition of the non-solvent, including the addition of an emulsifier to the non-solvent, the processing temperature, the rate of solvent evaporation, the rate of mixing, and the physical and chemical properties of the substance to be encapsulated. The optimum conditions can be determined empirically by one skilled in the art.

Examples demonstrate the production of multilayered microcapsules composed of polystyrene and ethylene vinyl acetate, polyanhydride and polystyrene, and polyanhydride and polylactic acid.

DETAILED DESCRIPTION OF THE INVENTION

Figure 1:
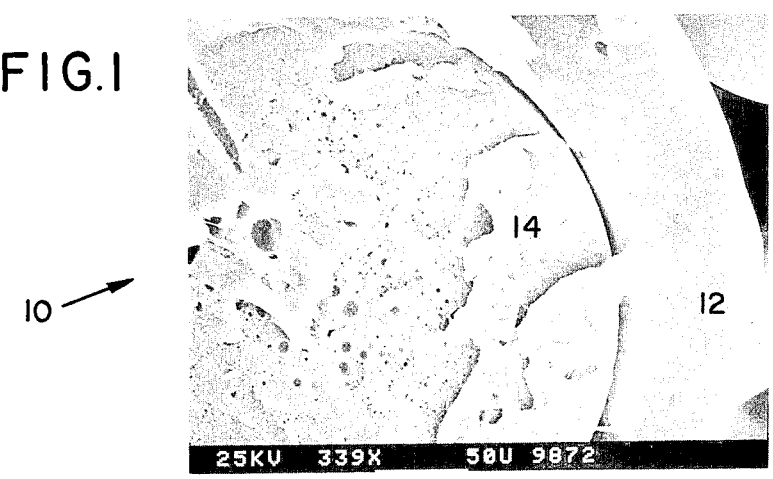
FIG. 1 is a photomicrograph of a microcapsule having a polystyrene layer and an ethylene vinyl acetate layer, in cross-section, made according to the method of the present invention.

The method of the present invention is described in detail as follows.

Selection of polymer

The polymers are selected on the basis of their physical and chemical properties, especially their degradation characteristics in vivo when used in biomedical applications.

Factors which must be taken into consideration in the selection of the polymer include the purity of the polymer, its molecular weight, and its solubility in organic and inorganic solvents. There are a variety of polymers which can be used in the method of the present invention.

The preferred biodegradable polymers are those which display surface erosion and linear release, polyanhydrides. Poly[bis(p-carboxy-phenoxy)propane anhydride](CPP) copolymerized with sebacic acid (SA), (pCPP:SA, 20:80) and (pCPP:SA, 50:50) and CPP copolymerized with dodecanedioic acid (DD), (pCPP:DD, 20:80) and (pCPP:DD, 50:50), and other similar copolymers, have been demonstrated to be useful in both in vivo and in vitro systems. Higher molecular weight polymers of high purity are preferred for use in drug delivery due to their favorable mechanical properties. Other useful biodegradable polymers include polylactic acid, polyorthoesters, and ethylene vinyl acetate. Polylactic acid rapidly degrades in vivo after a relatively long lag period. Polyorthoester is particularly resistant to degradation in vivo. Ethylene vinyl acetate has been approved by the FDA for use in vivo.

Preferred non-degradable polymers include polystyrene, polybutadiene, polyurethane, and polyamide.

Selection of the Solvents

The solvents must be chosen in conjunction with the polymers so that the polymers to be incorporated into the microcapsules will initially go into solution and then separate into distinct phases. The solvents must also be easily evaporated when non-solvent is added to the polymer-solvent mixture. Most of the polymers can be dissolved in a volatile organic solvent such as methylene chloride. The choice of solvent will also be dependent on the substance to be incorporated into the polymers since some may have a detrimental effect on biological activity.

Selection of the Substance to be Incorporated

Examples of substances which can be incorporated include drugs, fertilizers, insecticides, chemical indicators or dyes, chemical reactants and scents or flavorings Drugs which can be delivered by means of the present invention include insulin and heparin. The substance to be incorporated must not be adversely affected by the polymer solvent or the temperature at which solvent evaporation occurs. It is preferably provided in solution or in a particle size small enough to avoid "channeling" within the polymer. This is generally in the range of 50 microns or less. The substance can be soluble in the organic solvent. Purity and molecular weight of the substance, as well as its solubility in the polymer solutions, are factors to consider in optimizing the method.

Mixing of the Polymer Solutions with the Substance to be Incorporated

The polymers may be combined with the substance to be incorporated in either of two ways. In one method, each polymer is dissolved separately and the solutions combined. In the second, both polymers are simultaneously dissolved in one volatile organic solvent. The ultimate dispersion of the substance within the polymeric microcapsules is determined in part by the method of dissolution and combination. The substance to be incorporated can be added directly to one or both of the polymer solutions or to the mixture.

The polymers are mixed together using conventional means such as an overhead stirring device. The rate of stirring has a definite effect on the formation of the polymer layers and should be optimized for each polymer-solvent mixture.

Suspension of the Polymer solution in a Nonsolvent and Evaporation

The polymer solution is suspended in a nonsolvent, preferably an aqueous solution containing between 0 and 10% surface active agent, most preferably between 1 and 2% surface active agent. Useful surface active agents include polyvinyl alcohol, gelatin, and other surfactants and emulsifiers known to those skilled in the art.

The solvent(s) are then slowly evaporated. Vacuum evaporation or lyophilization may be employed, as well as other methods known to those skilled in the art. Temperatures of less than 60° C. are preferred due to the labile nature of many drugs with biological activity.

It is critical to control the rate of evaporation, as well as the parameters previously discussed, for one polymer solution to form a layer around a core of another polymer solution. However, the effect of the rate of evaporation on polymer layer formation may be used to advantageously modify the final product. For example, increasing the rate of evaporation causes the formation of spheres of the first polymer within the second polymer layer. By increasing the rate of evaporation still further, no inner layer is formed and all of the first polymer is present in spherical form within the second polymer layer. The inclusion of the spheres may be useful in forming "channels" of a biodegradable polymer such as polyanhydride within an outer layer of a non-degradable polymer such as polystyrene.

Additional Polymer Layers

Although more than two polymers can be layered using the above techniques, the complexity of the process dramatically increases with each additional polymer. It is therefore preferred to add other layers using methods known to those skilled in the art such as the hot melt technique.

The present invention is further described by the following non-limiting examples.

EXAMPLE 1

One g of polystyrene was dissolved in 5 ml methylene chloride. 1 g of ethylene vinyl acetate (EVA) was dissolved in 5 ml methylene chloride. The two solutions were mixed together, suspended in an aqueous solution, and the solvent evaporated. Two well defined layers appear which are the result of one polymer solution engulfing the other. After 5 hours the microspheres are washed and dried. FIG. 1 is a cross-sectional view of a microsphere 10 having a well-defined outer layer 12 and an inner layer, 14.

EXAMPLE 2

Figure 2:
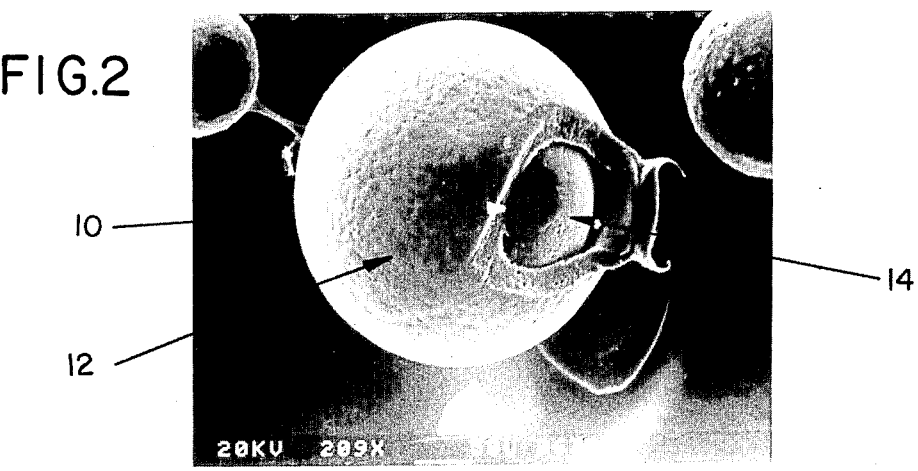
FIG. 2 is a perspective photomicrograph of microspheres having a polyanhydride layer and a polystyrene layer, made according to the method of the present invention.

The same method was used as in Example 1 with polystyrene and polyanhydride as the polymers. As shown in FIG. 2, the microspheres 10 consist of an inner core 14 and outer layer 12. As determined by infrared spectroscopy, the internal core 14 consists of the polyanhydride.

EXAMPLE 3

Figure 3:
FIG. 3 is a photomicrographs of a microsphere having a polylactic acid layer and a polyanhydride layer, in cross section, made according to the method of the present invention.

The same method was again used but with polylactic acid and polyanhydride polymers. Methyl red was dispersed within both polymers. The microspheres 10 having an internal layer 14 and outer layer 12 are shown in cross-section in FIG. 3.

Figure 4:
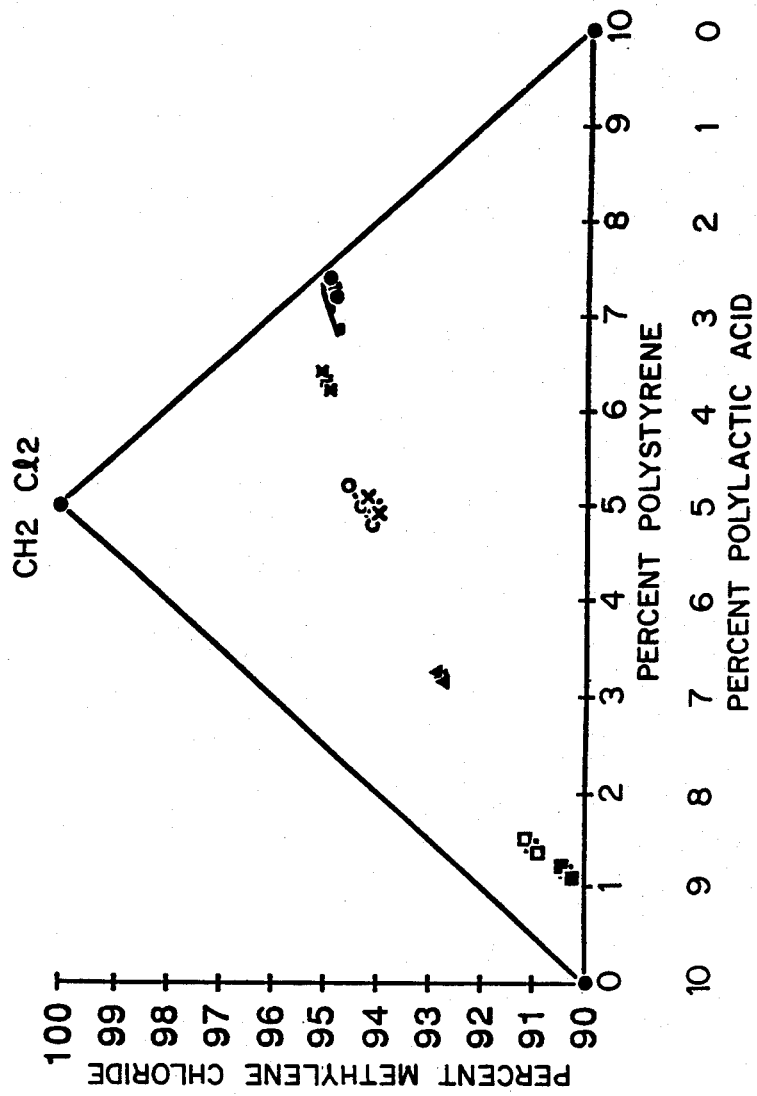
FIG. 4 is a phase diagram of the percent methylene chloride versus the percent polylactic acid and percent polystyrene in a methylene chloride mixture, where the relative percentages within the area below the curve are at the ratios which separation of the polymers occurs.

The separation of the two polymer phases is predicted on the basis of the phase diagram for the two polymers. When the polymers are at a ratio underneath the separation curve for the polymer-solvent mixture, the polymers form distinct phases. The phase diagram for polystyrene-polylactic acid polymers in methylene chloride is shown in FIG. 4. Experimental data is plotted for mixtures of polystyrene with polylactic acid in methylene chloride. Separation into two distinct phases occurred in all cases. Since the relative ratios are all under the separation curve, one is assured of obtaining two separate layers of polymers.

Polyorthoester- polylactic acid and polystyrene-polylactic acid polymer microcapsules have also been made using the method of Examples 1, 2, and 3, above.

Modifications and variations of the method of the present invention will be obvious to those skilled in the art from the foregoing detailed description and examples. One skilled in the art will also be able to optimize the method of the present invention for particular polymer and substance mixtures from the foregoing detailed description of the invention and examples. It is intended that such modifications, variations, and optimizations will come within the scope of the appended claims

We claim:

1. A method for forming multi-layered polymeric microcapsules comprising:
    selecting first and second polymers, wherein the polymers are selected from the group consisting of polyanhydrides, polyorthoesters, polylactic acid, polystyrene, polyamides, ethylene vinyl acetate, polybutadiene, polyurethanes, and copolymers and combinations thereof, to form microcapsules;
    selecting a substance to be incorporated into said microcapsules;
    dissolving said polymers in a volatile solvent;
    adding the substance to the polymer solution;
    mixing the polymer and substance solution;
    suspending the polymer substance mixture in a nonsolvent wherein said polymers separate into distinct phases; and
    evaporating the volatile solvent to form microcapsules having at least one distinct polymer layer around a polymer core.

2. The method of claim 1 wherein the polymers are selected from the group consisting of polyanhydrides, polyorthoesters, polylactic acid, polystyrene, polyamides, ethylene vinyl acetate, polybutadiene, polyurethanes, and copolymers and combinations thereof, wherein the polymers separate on the basis of differences in molecular weight.

3. The method of claim 1 wherein the volatile solvent is an organic solvent.

4. The method of claim 1 wherein the first polymer is dissolved in a first solvent and the second polymer is dissolved in a second solvent prior to combining the polymers.

5. The method of claim 4 wherein a first substance to be incorporated is added to the first polymer solution.

6. The method of claim 5 wherein a second substance is added to the second polymer solution.

7. The method of claim 1 wherein the first and second polymers are dissolved together in a first solvent.

8. The method of claim 1 further comprising forming additional polymer layers around said microcapsules.

9. The method of claim 1 further comprising adding other polymers to the polymer-substance solution.

10. The method of claim 1 wherein said nonsolvent is an aqueous solution.

11. The method of claim 10 further comprising adding between 0 and 10% surface active agent to the aqueous solution.

12. The method of claim 11 wherein the surface active agent is an emulsifier.

13. The method of claim 1 wherein the volatile solvents are evaporated at a temperature between 0° C. and 60° C.

14. The method of claim 1 wherein said solvent is rapidly evaporated to form spheres of said first polymer within a layer of said second polymer.

* * * * *

UNITED STATES PATENT AND TRADEMARK OFFICE
CERTIFICATE OF CORRECTION

PATENT NO. : 4,861,627
DATED : August 29, 1989
INVENTOR(S) : Edith Mathiowitz, Robert S. Langer It is certified that error appears in the above-identified patent and that said Letters Patent is hereby corrected as shown below:

Col. 2, line 62, change --photomicrographs-- to "photomicrograph".

Col. 5, line 43, insert "." after --claims-- to read "appended claims."

Signed and Sealed this

Twenty-fourth Day of May, 1994

Attest:

BRUCE LEHMAN

*Attesting Officer*     *Commissioner of Patents and Trademarks*